United States Patent [19]
Falwell et al.

[11] Patent Number: 5,685,878
[45] Date of Patent: Nov. 11, 1997

[54] SNAP FIT DISTAL ASSEMBLY FOR AN ABLATION CATHETER

[75] Inventors: Gary S. Falwell, Manchester; Russell F. Collins, Sandown, both of N.H.; Charles A. Gibson, III, Malden, Mass.

[73] Assignee: C.R. Bard, Inc., Murray Hill, N.J.

[21] Appl. No.: 555,847

[22] Filed: Nov. 13, 1995

[51] Int. Cl.$^6$ .................................................. A61B 17/36
[52] U.S. Cl. ................................ 606/49; 606/41; 606/1; 128/642
[58] Field of Search ........................... 128/642; 604/95; 607/98, 99, 119, 122; 606/41, 49, 1

[56] References Cited

U.S. PATENT DOCUMENTS

| | | |
|---|---|---|
| 2,688,329 | 3/1954 | Wallace . |
| 4,327,747 | 5/1982 | Gold ........................... 607/119 |
| 4,576,177 | 3/1986 | Webster, Jr. ..................... 128/660 |
| 4,657,016 | 4/1987 | Garito . |
| 4,785,815 | 11/1988 | Cohen .......................... 128/642 |
| 4,920,980 | 5/1990 | Jackowski ..................... 607/123 |
| 4,934,340 | 6/1990 | Ebling et al. ................... 604/95 |
| 4,936,842 | 6/1990 | D'Amelio et al. . |
| 4,960,134 | 10/1990 | Webster, Jr. ................... 607/116 |
| 5,239,999 | 8/1993 | Imran .......................... 128/642 |
| 5,257,635 | 11/1993 | Langberg ....................... 607/122 |
| 5,315,996 | 5/1994 | Lundquist ...................... 128/642 |
| 5,318,525 | 6/1994 | West et al. ..................... 604/95 |
| 5,348,481 | 9/1994 | Ortiz .......................... 128/642 |
| 5,363,861 | 11/1994 | Edwards et al. .................. 607/122 |
| 5,395,329 | 3/1995 | Fleischhacker et al. ............. 604/95 |
| 5,398,683 | 3/1995 | Edwards et al. .................. 128/642 |
| 5,413,508 | 5/1995 | Obara .......................... 128/642 |
| 5,417,208 | 5/1995 | Winkler ........................ 607/98 |
| 5,514,172 | 5/1996 | Mueller ........................ 607/119 |

FOREIGN PATENT DOCUMENTS

WO 92/02272  2/1992  WIPO .

OTHER PUBLICATIONS

GE Plastics *ULTEM Polyethermide Resin* Properties Guide, 8 pages.

PCT International Search Report, Mar. 10, 1997.

*Primary Examiner*—Michael Buiz
*Assistant Examiner*—Patrick W. Rasche
*Attorney, Agent, or Firm*—Darby & Darby

[57] ABSTRACT

A snap-fit assembly for the distal tip of a catheter is provided. The assembly includes a thermally insulative core and a thermally conductive ablation electrode arranged to interlock with one another by snapping the two together. The core has a proximal end which is shaped to readily fit within the distal tip of an ablation catheter and includes a head which temporarily compresses as it is inserted into the ablation electrode. A method of making the distal tip assembly is also provided.

20 Claims, 4 Drawing Sheets

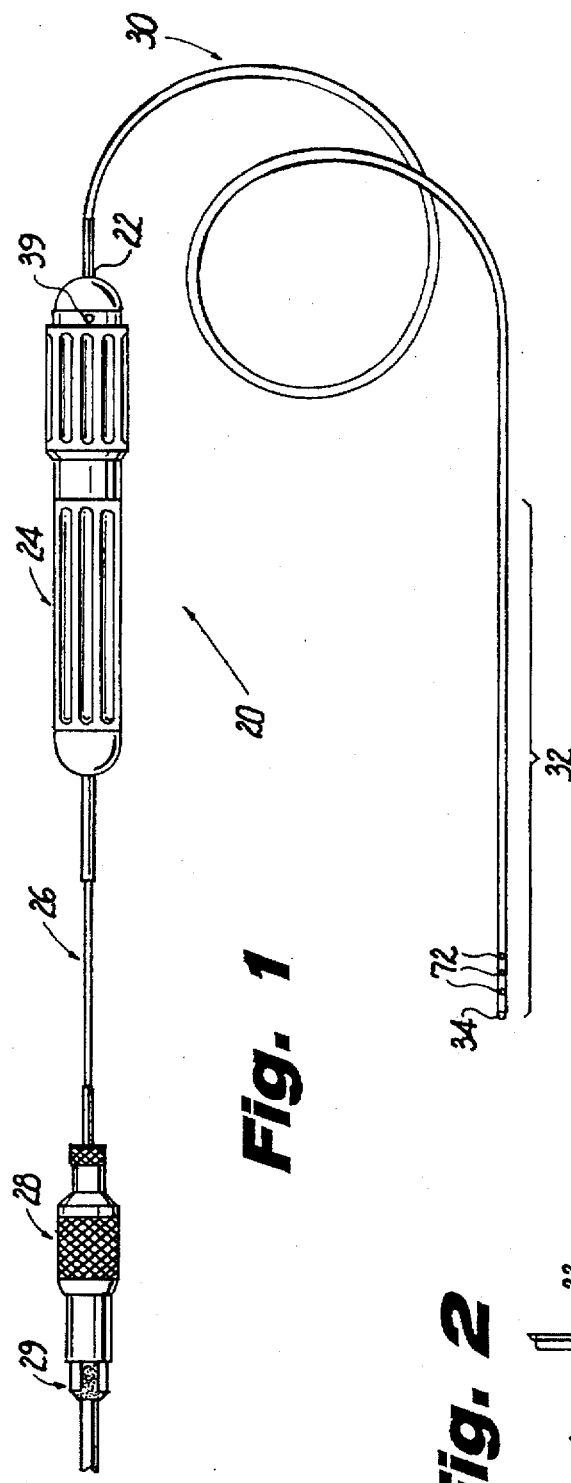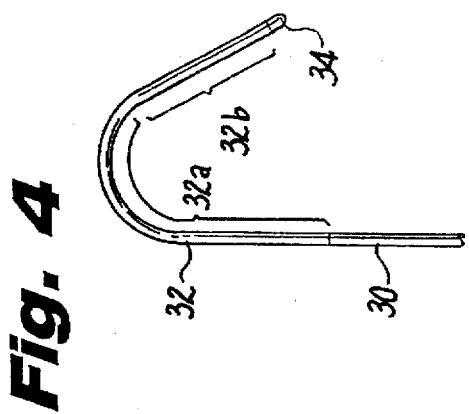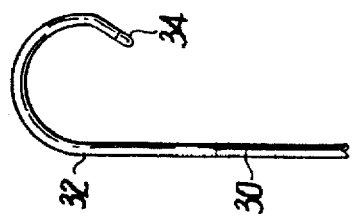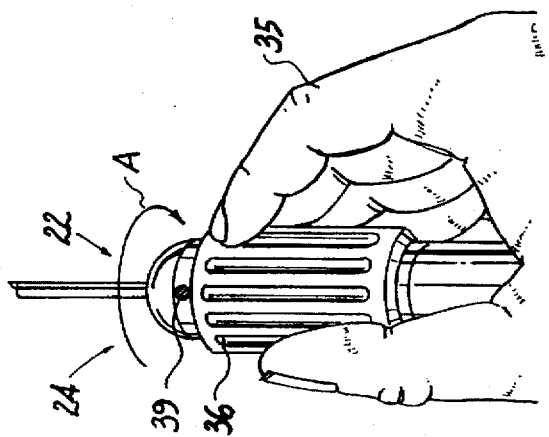

SNAP FIT DISTAL ASSEMBLY FOR AN ABLATION CATHETER

FIELD OF THE INVENTION

This invention relates to ablation catheters, and, more particularly, to a distal tip assembly for a steerable ablation catheter.

BACKGROUND OF THE INVENTION

One clinical role of endocardial catheter recording and mapping is to direct ablation therapies in the treatment of supraventricular tachycardia, ventricular tachycardia, atrial flutter, atrial fibrillation and other arrhythmias. Once an arrhythmogenic site has been localized and accessed, electrical energy shocks are applied to the endomyocardium to ablate arrhythmogenic regions and produce scars which interrupt the reentrant conduction pathways.

Conventional ablation catheters have an ablation electrode at their distal tip. A second electrode is provided either as a backplate in contact with a patient's skin or on the catheter itself, just proximal to the tip electrode. Ablation is effected by applying energy to an electrode once the electrode is in contact with the cardiac tissue. The energy can be, for example, radiofrequency (RF), direct current, ultrasound, microwave, or laser radiation. The ablation energy may be in the range of about ten to sixty Watts, at temperatures approaching 100° C. The electrode temperature is monitored in some catheter designs to prevent fouling of the ablation electrode. Nevertheless, the heated tip electrode can cause the distal end of the catheter to melt and possibly adhere to the patient.

In this regard, Jackowski has proposed in U.S. Pat. No. 4,920,980 seating the electrode within a refractory, insulative material at the catheter distal end. However, the body of the tip electrode extends into the soft tip of the catheter. As a result, the catheter tip is still subject to melting unless a high-melt temperature material is used. West et al. have proposed in U.S. Pat. No. 5,318,525 a catheter construction having the tip electrode bonded to a ceramic anchor which is in turn bonded to the catheter distal end. The West et al. distal assembly is complex and difficult to assemble.

OBJECTS AND SUMMARY OF THE INVENTION

It is an object of the invention to provide a tip electrode assembly for an ablation catheter which insulates the catheter from ablation temperatures.

It is another object of the invention to improve the temperature response of an ablation catheter tip electrode.

It is a further object of the invention to provide a distal tip assembly which is easy to assemble.

According to one aspect of the invention, a snap-fit assembly for the distal tip of a catheter is disclosed which includes a thermally insulative core and a thermally conductive ablation electrode arranged to interlock with one another by snapping the two together. The core has a proximal end which is shaped to readily fit within the distal tip of an ablation catheter.

The core includes a head which temporarily compresses as it is inserted into the ablation electrode. In the preferred embodiment, the core and ablation electrode are arranged so that the head is received in an internal groove of the ablation electrode, and so that continued insertion of the head causes the head to snap to at least a partially uncompressed state whereby the core and the ablation electrode are interlocked.

According to another aspect of the invention, an assembly for the distal tip of an ablation catheter is disclosed which includes a steering wire anchored to a thermally insulative core member which supports an ablation electrode. A pressure reducing device is provided to alleviate pressure applied to the core when a pulling force is applied to the steering wire.

According to yet another aspect of the invention, a method of making a distal tip electrode assembly for an ablation catheter is disclosed. The method includes the steps of affixing a conductive wire to a hollow ablation electrode, providing a thermally insulative core which includes a compressible head, and snapping the ablation electrode and the compressible head of the core together. According to more detailed aspects of the method, one or more additional steps may be performed such as affixing a temperature sensor to the hollow ablation electrode, or anchoring a steering wire to the core.

These and other features and advantages of the invention will be readily apparent from the following detailed description of a preferred embodiment taken in conjunction with the accompanying unscaled drawings.

BRIEF DESCRIPTION OF THE DRAWINGS

FIG. 1 is a plan view of a steerable ablation catheter fitted with a distal assembly according to the invention;

FIG. 2 is a detailed perspective view of a control handle that may be used to steer the catheter of FIG. 1;

FIG. 3 is a plan view of the distal end of the catheter of FIG. 1 having a predetermined radius of curvature;

FIG. 4 is a plan view of the distal end of the catheter of FIG. 1, as modified to have a generally linear configuration distal to a predetermined radius of curvature;

DETAILED DESCRIPTION OF PREFERRED EMBODIMENTS

Figure 5:
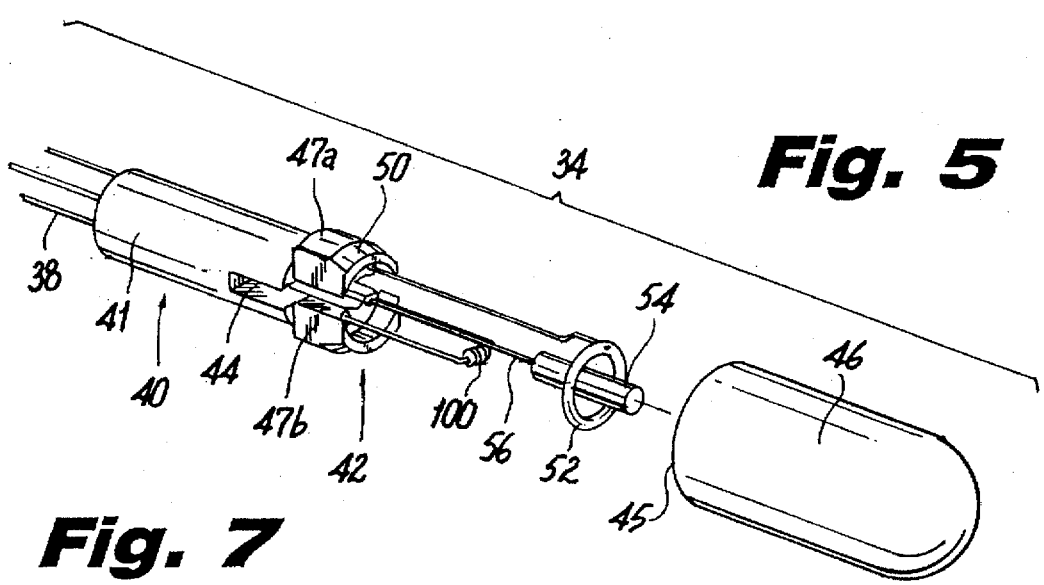
FIG. 5 is an exploded perspective view of the distal tip assembly of FIG. 1.

By way of overview and introduction, FIG. 1 illustrates a steerable ablation catheter 20 fitted with a snap-fit distal assembly 34 according to the invention. The catheter 20 includes a control handle 24 from which electrical wires 26 extend to a proximal connector 28. The catheter comprises a flexible, elongate shaft 30 which has a comparatively flexible distal segment or tipstock 32 connected to its distal end in conventional fashion. The shaft 30 and tipstock 32 are intended to be advanced through a patient's vasculature in conventional manner to the site to be treated. The catheter preferably has an overall length of approximately 115 cm for use in cardiac ablation procedures with the tipstock 32 extending from about four and a half to seven centimeters so that the catheter may be advanced through the femoral vein to a chamber within the heart, while the control handle 24 remains outside the patient to be manipulated by an operator 35. Different shaft 30 and tipstock 32 lengths would be chosen based on the procedure to be performed, the location at which the catheter is to be percutaneously introduced, and the anticipated path along which the shaft 30 must be steered. Preferably, the shaft 30 and tipstock 32 are made of a polyurethane tubing, the shaft 30 including a woven braid within the tubing to enhance stiffness and impart greater column and torsional strength to the shaft.

The electrical wires 26 include conductive leads from a plurality of electrodes, temperature sensors, other electronic devices which may be included in catheter 20, or any combination of the above. The electrical wires 26 provide electrical signals to electronic components such as electrocardiogram ("ECG") monitoring equipment and RF energy sources directly through the connector 28, or through an intervening patient cable 29 (shown broken away).

A knob 36 on the control handle 24 is rotatable relative to the handle (FIG. 2) by the operator to cause a slideblock (not shown) within the control handle 24 to move away from a proximal end 22 of the shaft 30. A steering wire 38, which is slidably housed within the tipstock 32 and the shaft 30 (see FIG. 6A), is secured at its proximal end to the slideblock. The steering wire 38 is pulled proximally due to rotation of the knob 36, for example, in the direction of arrow A (FIG. 2). Conversely, the steering wire 38 advances distally when the slideblock moves toward the proximal end 22 of the shaft 30 as a result of rotation of the knob 36 in the opposite direction. The control handle 24 may be as described in U.S. patent application Ser. No. 08/518,521, filed Aug. 23, 1995 for Steerable Electrode Catheter to Bowden et al., the disclosure of which is hereby incorporated by reference as if set forth fully herein.

The steering wire 38 extends distally from the slideblock, through the shaft 30, to the distal tip assembly 34 where it is anchored, as described more fully below. Because the steering wire 38 is anchored to the distal tip assembly 34, a proximal pulling force on the steering wire 38 causes the tipstock 32 to deflect in a single plane and with a radius of curvature which is determined by the length and compressive strength of the tipstock 32, as shown in FIG. 3. The radius of curvature may be in the range of about two to four and a half centimeters. The steering wire 38 must have a tensile strength sufficient to overcome the compressive strength of the tipstock 32 to cause the tipstock 32 to deflect. When the knob 36 is rotated in a direction opposite to arrow A, the compressive forces on the tip stock are released to cause the catheter tip to return to its undeflected state. In the preferred embodiment, the steering wire 38 is a stainless steel wire having a pull strength of about 15.5 pounds.

Figure 8:
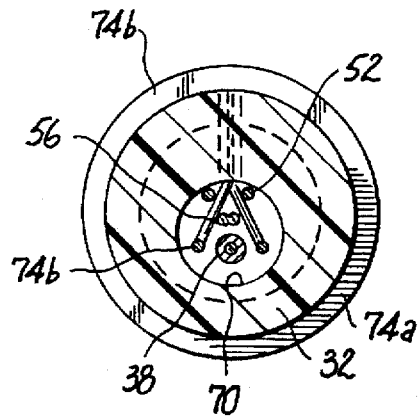
FIG. 8 is a cross sectional view substantially taken along line 8—8 of FIG. 6A.
Figure 6A:
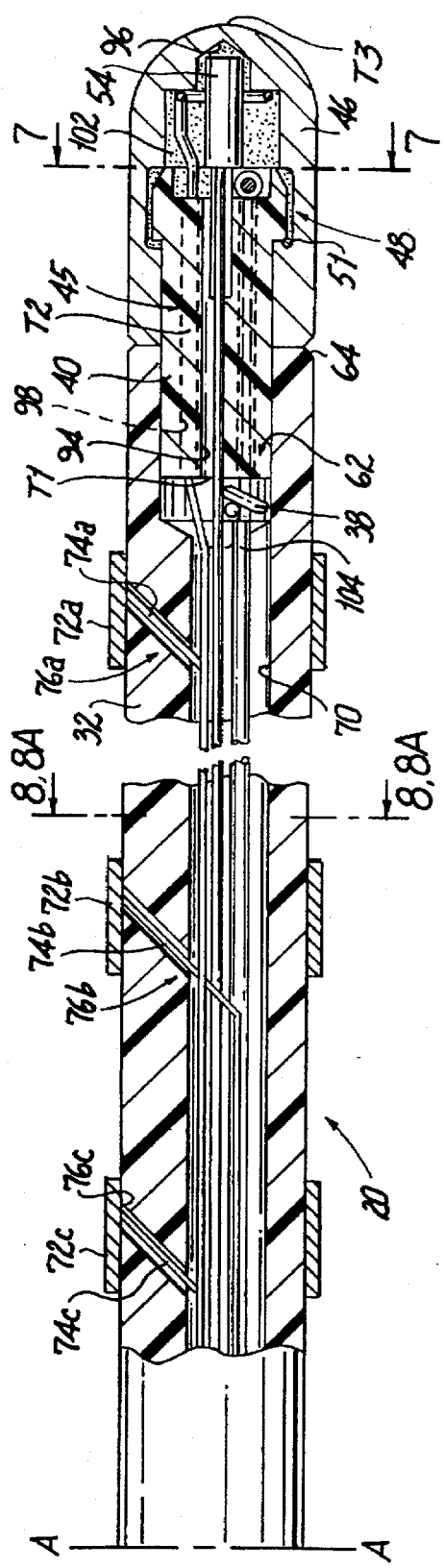
FIG. 6A is an elevational view, partially in section, of the catheter of FIG. 1.

The steering wire 38 is preferably guided eccentrically with respect to the longitudinal axis of the catheter 20, and more preferably guided eccentrically within the tipstock 32, so that the tipstock 32 will favor deflection in a known plane due to a wall thickness differential on either side of the steering wire 38 in the tipstock 32 (see FIGS. 6A and 8). The entire control handle 24 can be torqued by the operator 35 to steer the shaft 30 through the patient's vasculature. Additional steering wires can be provided, and a radius of curvature adjusting means can be provided in the manner described in the aforementioned U.S. patent application Ser. No. 08/518,521.

In FIG. 4, the shaft 30 has been modified to include a hypotube 37 at its distal end which serves as a rigidifying element, for example, just proximal to the distal tip assembly 34 (FIG. 8a), so that rotation of the knob 36 causes deflection of the tipstock 32 with the distalmost portion 32b of the tipstock 32 remaining generally straight. A proximal portion 32a of the tipstock 32 which is clear of the hypotube 37 assumes a curve of a predetermined radius based on its length and its compressive strength. The hypotube 37 preferably extends about one to three centimeters along the catheter 20 and may be anchored to the steering wire 38, the distal assembly 34, or the distal most portion 32b of the tipstock. A stiffening wire or similar rigidifying element can be used in lieu of the hypotube 37.

The knob 36 preferably includes an indicator 39 which indicates that the knob has been rotated from its neutral position (where no force is applied to the steering wire 38). This means that a pulling force is being applied to the steering wire 38 and that the tipstock 32 is being deflected. The indicator 39 may be a tab affixed to the upper margin of the knob 36 which is visible through an aperture in the control handle 24 only when, for example, the slideblock is in a position proximate the proximal end 22 of the shaft 30. In this state, the tab is visible and indicates that no pulling force is being applied to the steering wire 38. Rotation of the knob 36 from the neutral position moves the indicator 39 out of registry with the aperture which indicates to the operator that a pulling force is being applied to the steering wire 38. The indicator and knob are preferably molded from a plastic material having a color which differs from that of the remainder of the control handle 24.

Turning now to FIG. 5, an exploded perspective view of the distal tip assembly 34 is shown. The distal assembly 34 comprises a core 40 which has a proximal portion 41 adapted to be received in the distal tip 64 of the tipstock 32, and a compressible head 42 at its distal end. The compressible head 42 includes anchor tabs 47a, 47b. The core 40 has a longitudinal slot 44 extending proximally from its distal face which permits the anchor tabs 47a, 47b to resiliently flex toward each other as the core 40 is received within an aperture 45 in a hollow ablation electrode 46 (FIG. 6A). Continued insertion of the core 40 into the ablation electrode 46 causes the anchor tabs 47a, 47b to snap into a groove 48 in the ablation electrode 46 which locks the core 40 and the ablation electrode 46 together. Due to tolerance control or other design considerations, the head 42 may remain in a partially compressed state even after the core and ablation electrode have snapped together so long as the two components interlock. The compressible head 42 includes a chamfered leading edge 50 which facilitates insertion of the core 40 into the aperture 45 of the ablation electrode 46 by camming the anchor tabs 47a, 47b together and thereby compressing the head 42 to a reduced profile. The groove 48 has a shoulder 51 at its proximal edge which prevents the core 40 from being withdrawn from the ablation electrode 46 once the anchor tabs 47a, 47b have snapped into the groove 48 (FIG. 6A).

Figure 11:
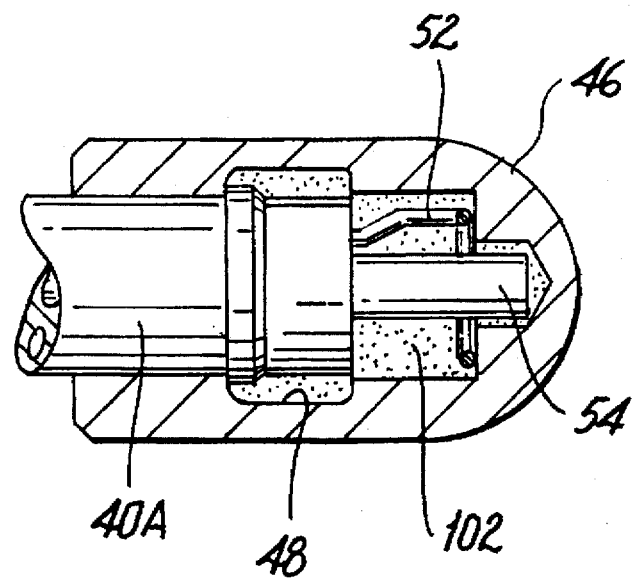
FIG. 11 is a side elevational view, partially in section, showing an alternative configuration of the distal tip assembly of FIG. 1.

Alternatively, the core 40 and ablation electrode 46 may include a ratchet and pawl arrangement, or a generally annular projection made of an intrinsically compressible plastic such as polycarbonate or ULTEM®, shaped to mate with the groove 48 in the ablation electrode 46. For example, the annular projection may project about one to three mils on either side of the core 40A, and the groove 48 in the ablation electrode 46 may be sized to receive the annular projection in an uncompressed state, as shown in FIG. 11. All that is important in these alternative configurations is that the core 40 and ablation electrode 46 interlock via a snap action.

The core 40 is preferably made of a material having a low temperature coefficient, such as the ULTEM® 1000 resin produced by the GE Plastics division of the General Electric Company, Pittsfield, Mass. The low temperature coefficient material provides thermal insulation between the ablation electrode 46 and the tipstock 32, and, preferably, the core 40 has a lower thermal mass than the ablation electrode. The provision of the core 40 between the tipstock 32 and the ablation electrode 46 reduces the likelihood of catheter damage during an ablation procedure which better ensures that a single catheter can be used for a given procedure, or perhaps reused (once sterilized) in subsequent procedures. The cap electrode 46 and the distal tip 64 of the tipstock 32 may be spaced from each other once the core 40 has been mounted in the distal tip 64 by a thin bead of epoxy, or by an annular ring on the core 40, disposed between its proximal end 41 and the compressible head 42. Further, a wider range of materials can be selected for the tipstock 32, including materials with melt-temperatures that are significantly less than the expected ablation temperature, such as polyurethane.

Empirical tests were made using 45 watts of ablation power with temperature measurements being taken by thermocouples located at three points on the distal assembly 34, as shown in FIG. 6A, with the distal assembly 34 disposed in a 37° C. water bath, pressed against a sponge to simulate body tissue. A ground plate was positioned on the opposite side of the sponge. Thermocouple T1 was positioned at the proximal face of the core 40. Thermocouple T2 was positioned within an off-axis lumen 98 in the core 40, at the proximal end of the ablation electrode 46. And Thermocouple T3 was positioned at the distal tip of the ablation electrode 46. The results of these measurements are as follows:

| Thermocouple Position | Time | | |
| --- | --- | --- | --- |
| | 40 sec | 48 sec | 50 sec |
| T1 | 55° C. | 56° C. | 56° C. |
| T2 | 57° C. | 58° C. | 58° C. |
| T3 | 95° C. | 95° C. | 95° C. |

As can be appreciated from the table above by comparing the temperatures measured at T1 and T2 to T3, the core 40 within the distal tip 64 insulates the bore 62 of the distal tip from the temperatures seen at the energized ablation electrode 46 (T3) over a time period which approximates or exceeds that of a typical cardiac ablation procedure. If the ablation electrode 46 instead extended into the bore 62 as in conventional designs, then the distal tip 64 would more closely approximate the 95° C. temperature of the ablation electrode 46. A moderate rise in the temperature of the core 40 is also indicated in the above table; however, the core's temperature remains significantly lower than the temperature of the ablation electrode In addition, the reduced thermal mass of conductive material in the ablation electrode 46 as compared to solid platinum electrodes in conventional ablation catheter designs provides an improved temperature response time with regard to the speed that the ablation electrode is raised to the desired ablation temperature and, because of the insulative core 40, provides an improved speed at which the temperature of the ablation electrode can be regulated. In particular, the core does not readily heat by convection and thereby restricts the heat to the ablation electrode 46 itself, and the patient's blood flow provides a continuous source of comparatively cool fluid (37° C.) to assist in reducing the ablation electrode 46 temperature to provide the operator with better control over the ablation procedure. Thus, the snap fit assembly allows a rapid rise to the desired ablation temperature, and a rapid monitoring and regulation of the actual ablation electrode temperature as compared to known designs. Preferably, the ablation electrode 46 is made of platinum.

With further reference to FIGS. 5 and 6A, the distal assembly 34 preferably serves as an anchor for the steering wire 38 and also preferably houses a temperature sensor 54. The core 40 includes a central lumen 94 and several off-axis lumens 98 for conveying wires 52, 56 from the ablation electrode 46 and temperature sensor 54, respectively, to the connector 28. The temperature sensor 54 is preferably a thermistor and may be positioned within a cavity 96 in the ablation electrode 46 about four to seven mils from the ablation electrode distal tip. A potting compound 102, for example, TRA-BOND FDA-2 epoxy made by Tra-Con, Inc. of Medford, Mass. may add rigidity to the entire distal assembly 34, as described below.

In FIG. 6A, there is seen a central bore 62 at the distal tip 64 of the tipstock 32. The central bore 62 is sized to fit the proximal end of the core 40. The tipstock 32 defines a lumen 70 for receiving the steering wire 38 and a surrounding teflon sheath 104 (FIGS. 6A-9), the temperature sensor conductive wires 56, and the conductive wire 52 from the distal assembly 34. Mounted in spaced relation along the tipstock 32 are ring electrodes 72a, 72b, and 72c which may be sized for intracardiac ECG recording, mapping, stimulation, or ablation. Each ring electrode 72 may extend longitudinally about one half to four millimeters along the tipstock 32 from the ring electrode's proximal edge to its distal edge. The ring electrodes 72 are electrically connected to suitable components via conductive wires 74a, 74b, and 74c which extend through respective apertures 76a–c in the side of the tipstock 32 into the lumen 70.

The ring electrodes 72 may be spaced apart in the range of about one to five millimeters and may extend proximally sixty millimeters or more from the tip of the distal assembly 34 along the tipstock 32. For example, the ring electrode 74a may be two millimeters from distal tip 64 of the shaft 30, the ring electrode 74b may be spaced five millimeters from the proximal edge of the ring electrode 74a, and the ring electrode 74c may be spaced two millimeters from the proximal edge of the ring electrode 74b.

Figure 6B:
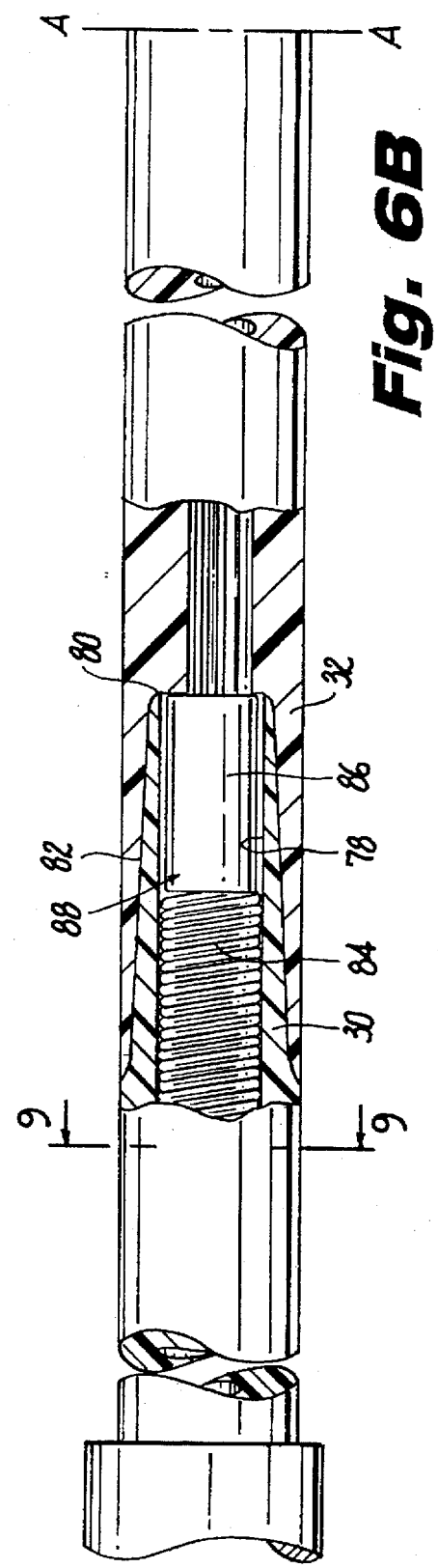
FIG. 6B is an elevational view, partially in section, of a more proximal portion of the catheter of FIG. 6A, and connects thereto along match line A—A.

The tipstock 32 is connected to the distal end of the shaft 30 in conventional manner, preferably along complementary tapered and overlapping regions at their distal and proximal ends, respectively, by ultrasonic welding (FIG. 6B).

The lumen 70 of the tipstock 32 and the throughlumen 78 of the shaft 30 are in communication with each other. The lumen 70 is preferably disposed eccentrically relative to the longitudinal axis of the tipstock 32, so that proximally directed forces applied to the steering wire 38 cause the tipstock 32 to favor deflection in a predictable, single plane. Also, the eccentric lumen 70 creates an abutment 80 in the vicinity of the union of the tipstock 32 and the shaft 30. In the preferred embodiment, a stiffening spring 84 extends from the proximal end 22 of the shaft 30 to the abutment 80. A stiffening tube 86 may be interposed between the distal end 88 of the stiffening spring 84 and the abutment 80.

Figure 7:
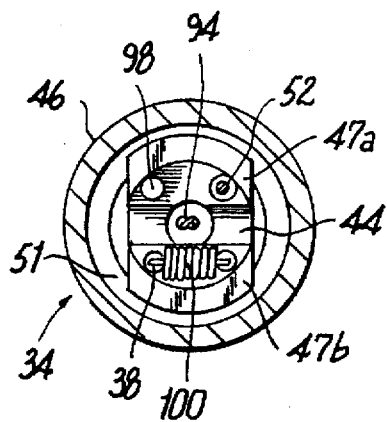
FIG. 7 is a cross sectional view substantially taken along line 7—7 of FIG. 6A.

With reference now to FIG. 7, the core 40 is interlocked to the ablation electrode 46, with the anchor tabs 47a, 47b of compressible head 42 snapped into the groove 48, just distal to the shoulder 51. The anchor tabs 47,a, 47b cannot be withdrawn beyond shoulder 51. Further, the steering wire 38 is shown looped through two of the off-axis lumens 98 in the core 40 and passing through a coil spring 100, which serves as a pressure reducing mechanism in the preferred embodiment to mitigate or eliminate a so called "cheese knife" effect in which the tensile force applied to the steering wire 38 causes the steering wire to cut into the distal face of the core 40. The coil spring 100 prevents the steering wire 38 from slicing the core by distributing a pulling force which may be applied to the steering wire 38 across the coils of the spring. Comparing FIGS. 6A and 7, the steering wire 38 is seen to extend distally through one of the lumens 98 in the core 40, through the spring 100, and back through another of the lumens 98, preferably, to a point proximal of the core 40 where it is wrapped around itself to form an anchor for the steering wire 38. Preferably, the steering wire 38 is wrapped at least two times about itself. Favorable results have also been observed where the steering wire 38 is arranged to pass through one of the lumens 98, through the spring 100, and then partially back through another of the lumens 98, with the steering wire soldered to the spring 100.

FIG. 8 illustrates the eccentric lumen 70 in the tipstock 32 which causes a pulling force, which may be applied to the steering wire 38 via the control handle 24, to be directed eccentrically within the tipstock 32. The eccentric lumen 70 provides a reduced thickness lumen wall on one side of the steering wire 38. Further, the off-axis lumens 98 about which the steering wire 38 is anchored better ensures that the tipstock 32 repeatedly deflects in a predictable plane for reliable steering of the distal end of the shaft 30.

Figure 8A:
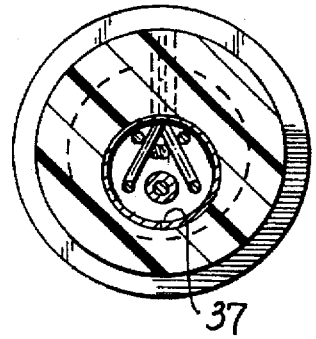
FIG. 8A is a cross sectional view substantially taken along line 8A—8A of FIG. 6A illustrating the catheter of FIG. 1 as modified to have a generally straight segment distal of a predetermined radius of curvature when steered.

In FIG. 8A, the shaft 30 includes the hypotube 37 within the tipstock distal portion 32b. The hypotube 37 causes the distal end of the catheter to retain a generally straight configuration even when a pulling force is applied (see FIG. 4).

Figure 9:
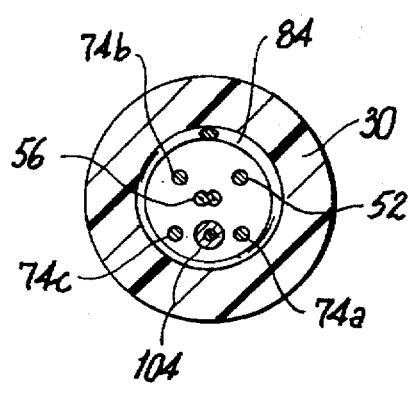
FIG. 9 is a cross sectional view substantially taken along line 9—9 of FIG. 6B.

FIG. 9 is a cross section taken through the shaft 30 and illustrates the steering wire 38, conductive wires 56, conductive wire 52, and conductive wires 74 from the ring electrodes 72 extending proximally within the stiffening spring 84 toward the control handle 24.

The assembly of the distal tip assembly 24 is as follows. The plastic core 40 is preferably injection molded. The ablation electrode 46 is machined to have the desired overall dimension for the size of catheter with which it is to be used. The machining is preferably performed under computer control using a machine that can select a first drill bit to generally hollow out the ablation electrode 46, then a second, smaller bit to define the cavity 96, and finally to form the groove 48 using a key cutter, for example, by circular interpolation as understood by those of ordinary skill in the art of machining.

Conductive wire 52 is preferably wrapped like a lasso and resistance welded to the ablation electrode 46. Next, an epoxy which is thermally but not electrically conductive, for example, STYCAST® 2850 FT Epoxy Encapsulant, preferably mixed with Catalyst 24LV, both made by Emerson & Cuming Composite Materials, Inc. of Canton, Mass., is inserted into the central cavity 96 and the temperature sensor 54 bonded therein. The conductive wires 52 and 56 from the ablation electrode 46 and the temperature sensor 54 are threaded through the lumens 98, 94, respectively, either before or after their attachment to the ablation electrode 46.

The steering wire 38 is attached to the core by threading it in a U-shape through lumens in the core. In particular, the steering wire 38 is threaded through one of the off-axis lumens 98, through the coil spring 100, and then through another of the off-axis lumens 98. The steering wire may extend to a point proximal of the core 40 at which location it may be wrapped about itself to complete its anchoring, or it may terminate after the U-shaped bend within one of the lumens 98 and instead be soldered or brazed to the coil spring 100. Preferably, a teflon coated steering wire 38 is selected, the portions of the steering wire 38 that are anchored to the core 40 and the control handle 24 preferably being stripped clear of the teflon. Alternatively, a lubricous sleeve such as teflon may be bonded to the steering wire 38 to reduce the frictional forces that are imparted by the walls of lumens 70, 78 when the steering wire is moved and electrically insulate the steering wire. A second steering wire 38A may be threaded through lumens 98 disposed on the opposite side of the central lumen 94.

After the conductive wire 52, the temperature sensor 54, and the steering wire 38 have been suitably attached, the ablation electrode 46 may be filled with a potting compound 102 such as FDA-2 epoxy and the core and ablation electrode snapped together in the manner previously described. The snap action of the core 40 and ablation electrode 46 is both audible and tactile. Further, the steering wire, thermistor wires, and ablation electrode wire are received without any twisting action unlike other known methods of making an ablation catheter. Moreover, the potting compound 102 electrically and thermally isolates the steering wire 38 from the ablation electrode 46.

Next, the steering wire 38, conductive wires 56, and conductive wire 52 may be threaded through the lumen 70 and throughlumen 78 to the control handle 24 to assemble the distal tip assembly 34 on the catheter 20. The proximal end of the core 40 can be coated with an epoxy prior to insertion into the central bore 62 at the distal end of the tipstock 32. A thin bead of epoxy (not shown) may space the cap electrode 46 from the distal tip 64 of the tipstock 32 when the distal assembly 34 is mounted to the catheter 20, or the core 40 may include an annular ring which spaces the ablation electrode 46 from the distal tip 64 when the core is inserted into the distal tip. The assembly is completed by attaching the steering wire 38 to the slideblock and the conductive wire 52, 56, and 74 to respective ones of wires 26.

The catheter 20 may be provided with a specified or predetermined radius of curvature which is achieved when the tipstock 32 is deflected. A particular catheter 20 can be made to assume a given radius of curvature, and a range of catheters 20, each having a different radius of curvature, can be provided to satisfy the requirements of particular procedures. Alternatively, a radius of curvature adjusting means can be provided in the manner described in the aforementioned U.S. patent application Ser. No. 08/518,521.

Any one or more of these alternative embodiments may be combined one with another for a particular use contemplated or intended for a tip deflectable, steerable ablation catheter.

Two or more slots 44 can be provided, although only one is illustrated in the figures.

A bearing plate (e.g., a washer) 100A or cylindrical element (e.g., a hypotube) can be brazed to or wrapped about the steering wire 38, instead of using the coil spring 100 as a pressure reducing mechanism, to provide a bearing surface against which the tensile forces are distributed. In this alternative construction, the distal end 42 of the core 40 is hollowed (see FIGS. 5 and 6A) to seat the bearing plate 100A proximal to the distal end of the anchor tabs 47a, 47b.

Figure 10:
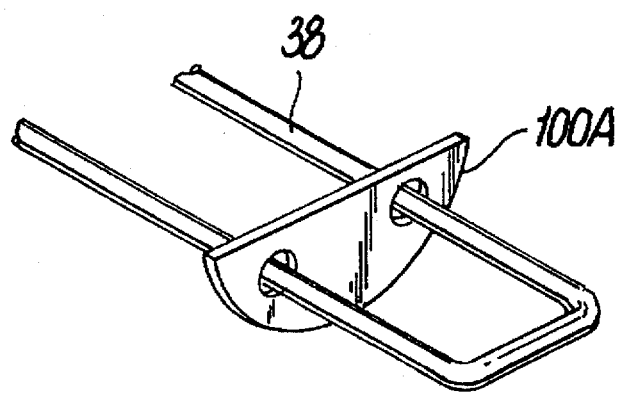
FIG. 10 is a perspective view of a modification of the preferred embodiment in which a bearing plate is provided instead of a coil spring.

Preferably, the bearing plate 100A comprises an apertured half-moon segment disposed on the distal end 42 of the core 40 on one of the anchor tabs 47a, 47b, as shown in FIG. 10. If a second steering wire 38A is provided, a second bearing plate 100A would be disposed on the distal end 42 of the core 40, on the other of the anchor tabs 47a, 47b. Preferably, the steering wire 38 is soldered or brazed to the bearing plate 100A. The bearing plate 100A is shaped to permit the anchor tabs 47a, 47b to flex as the core 40 is inserted into the ablation electrode 46.

As will be readily apparent to those skilled in the art the dimensions stated relate to one particular catheter size and are disclosed solely by way of example and should not, therefore, be understood as an intended limitation on the scope of the invention.

Furthermore, the particular features described above can be arranged on different elements to achieve a distal assembly within the spirit of the foregoing disclosure.

Having thus described a preferred embodiment of the present invention, it is to be understood that the above described device is merely illustrative of the principles of the present invention, and that other devices may be devised by those skilled in the art without departing from the spirit and scope of the invention as claimed below.

What is claimed is:

1. An assembly for a distal tip of an ablation catheter, comprising:
   a thermally insulative core having a proximal end and a distal end, the proximal end being shaped to fit within the distal tip of the ablation catheter and the distal end including a compressible head;
   a hollow ablation electrode including an aperture which is smaller than the compressible head; and
   snap-lock means for interlocking the compressible head of the core within the aperture of the ablation electrode.

2. The assembly as in claim 1, wherein the snap-lock means comprises an internal groove in the ablation electrode, the internal groove being sized to permit the compressible head to snap to at least a partially uncompressed state.

3. The assembly as in claim 2, wherein the compressible head includes an anchor tab, the compressible head adapted to snap to the at least partially uncompressed state when the anchor tab is received within the internal groove.

4. The assembly as in claim 3, wherein the internal groove includes a proximal shoulder which restrains proximal motion of the anchor tab when the compressible head is in the at least partially uncompressed state, whereby the compressible head and the ablation electrode are interlocked.

5. The assembly as in claim 1, wherein the compressible head includes a longitudinal slot extending proximally from the distal end of the core.

6. The assembly as in claim 1, wherein the core has a comparatively lower thermal mass than the ablation electrode.

7. The assembly as in claim 1, further comprising an elongate steering wire anchored to the core.

8. The assembly as in claim 7, further comprising a hollow pressure reducing means for reducing pressure applied to the core when a pulling force is applied to the steering wire.

9. The assembly as in claim 8, wherein the pressure reducing means is a coiled spring.

10. The assembly as in claim 8, wherein the core has a plurality of lumens and wherein the steering wire is anchored to the core by threading the steering wire through one of the plurality of lumens of the core, the pressure reducing means, and another of the plurality of lumens of the core.

11. The assembly as in claim 7, further comprising an elongate rigidifying means for rigidifying the distal tip of the ablation catheter and for preventing same from deflecting in response to any pulling force applied to the steering wire.

12. The assembly as in claim 1, further comprising an elongate steering wire anchored to the ablation electrode, and an elongate rigidifying means for rigidifying the distal tip of the ablation catheter and for preventing same from deflecting in response to any pulling force applied to the steering wire.

13. The assembly as in claim 1, further comprising a temperature sensor disposed within the ablation electrode.

14. A steerable ablation catheter, comprising:
   a steering wire having a proximal and a distal end;
   a shaft having a proximal end and a distal end and a throughlumen;
   a tipstock connected to the distal end of the shaft and extending to a distal tip, the tipstock having a lumen extending therethrough and communicating with the throughlumen of the shaft, the tipstock including means for guiding the steering wire eccentrically;
   a control handle attached to the proximal end of the shaft, the control handle including means for applying a pulling force to the steering wire proximal end; and
   a distal tip assembly connected to the distal tip of the tipstock and anchored to the steering wire distal end, the distal tip assembly including:
      a thermally insulative core having a proximal end and a distal end, the proximal end being shaped to fit within the distal tip of the ablation catheter and the distal end including a compressible head;
      a hollow ablation electrode including an aperture which is smaller than the compressible head; and
      snap-lock means for interlocking the compressible head of the core within the aperture of the ablation electrode.

15. The steerable ablation catheter as in claim 14, wherein the control handle includes indicating means for indicating whether a pulling force is being applied to the steering wire proximal end.

16. The steerable ablation catheter as in claim 14, further comprising a rigidifying means for rigidifying the distal tip of the ablation catheter and for preventing same from deflecting in response to any pulling force applied to the steering wire.

17. An assembly for the distal tip of an ablation catheter, comprising:
   a thermally insulative core having a proximal end and a distal end, the proximal end being shaped to fit within the distal tip of the ablation catheter;
   a hollow ablation electrode surrounding the distal end of the core;
   an elongate steering wire anchored to the core; and
   a pressure reducing means for reducing pressure applied to the core when a pulling force is applied to the steering wire.

18. The assembly as in claim 17, wherein the pressure reducing means is a coiled spring.

19. The assembly as in claim 18, wherein the core has a plurality of lumens and wherein the steering wire is anchored to the core by threading the steering wire through one of the plurality of lumens of the core, the pressure reducing means, and another of the plurality of lumens of the core.

20. The assembly as in claim 18, further comprising an elongate rigidifying means for rigidifying the distal tip of the ablation catheter and for preventing same from deflecting in response to any pulling force applied to the steering wire.

* * * * *